(12) United States Patent
Milkovich

(10) Patent No.: US 12,268,395 B1
(45) Date of Patent: Apr. 8, 2025

(54) VOLUNTARY EUTHANASIA DEVICE

(71) Applicant: John Milkovich, Butler, TN (US)

(72) Inventor: John Milkovich, Butler, TN (US)

( * ) Notice: Subject to any disclaimer, the term of this patent is extended or adjusted under 35 U.S.C. 154(b) by 0 days.

(21) Appl. No.: 18/629,289

(22) Filed: Apr. 8, 2024

(51) Int. Cl.
*A61B 17/132* (2006.01)

(52) U.S. Cl.
CPC ................ *A61B 17/1322* (2013.01)

(58) Field of Classification Search
CPC .......... A61B 17/1322; A61B 17/132; A61B 17/1325; A61B 17/135
USPC ............................................. 602/36; 128/845
See application file for complete search history.

(56) References Cited

U.S. PATENT DOCUMENTS

| | | | | |
|---|---|---|---|---|
| 764,704 A * | 7/1904 | Blagg | ................ | D06F 81/00 38/108 |
| 3,396,933 A * | 8/1968 | Ward | ................ | A47B 13/04 297/440.13 |
| 3,967,343 A * | 7/1976 | Westervelt | ........... | A22B 7/001 119/815 |
| 4,249,773 A * | 2/1981 | Giambalvo | ............. | A47B 3/14 108/174 |
| 4,498,425 A * | 2/1985 | Aanestad | ............... | A01K 15/04 119/729 |
| 5,018,785 A * | 5/1991 | Monson | ................ | A47B 3/14 108/162 |
| 7,597,615 B2 | 10/2009 | van den Nieuwelaar et al. | | |
| 8,216,031 B2 | 7/2012 | Kleinsasser | | |
| 10,993,528 B1 * | 5/2021 | Mackall, II | ......... | A47B 13/003 |
| 11,564,398 B2 * | 1/2023 | Christian | ........... | A22C 21/0046 |
| 11,805,894 B1 * | 11/2023 | Lin | ........................ | A47B 13/02 |
| 2011/0092145 A1 * | 4/2011 | Kleinsasser | ........... | A22B 3/086 452/52 |
| 2023/0407670 A1 * | 12/2023 | Graybill | ................. | A47C 4/286 |

\* cited by examiner

*Primary Examiner* — Tarla R Patel
(74) *Attorney, Agent, or Firm* — Sheri Higgins Law, PLLC; Sheri Higgins

(57) ABSTRACT

Many terminally ill people desire to end their lives on their own terms instead of waiting for the disease to take their lives. A voluntary euthanasia device can include a base, a vertical connector including a first end connected to the base and a second end connected to two compression arms. The compression arms can form a V shape with the vertical connector that receive a terminally ill person's neck. During use, blood flow is cut off to the brain by a pressure being exerted on the person's carotid arteries, and with sustained pressure results in the person's death. The device can be used in the person's home or any other location of their choosing.

19 Claims, 3 Drawing Sheets

VOLUNTARY EUTHANASIA DEVICE

TECHNICAL FIELD

Euthanasia devices can be used by a terminally ill person. The device is painless and can be used in the comfort of the person's home or other location.

BRIEF DESCRIPTION OF THE FIGURES

The features and advantages of the embodiments will be more readily appreciated when considered in conjunction with the accompanying figures. The figures are not to be construed as limiting any of the embodiments.

DETAILED DESCRIPTION

Figure 1:
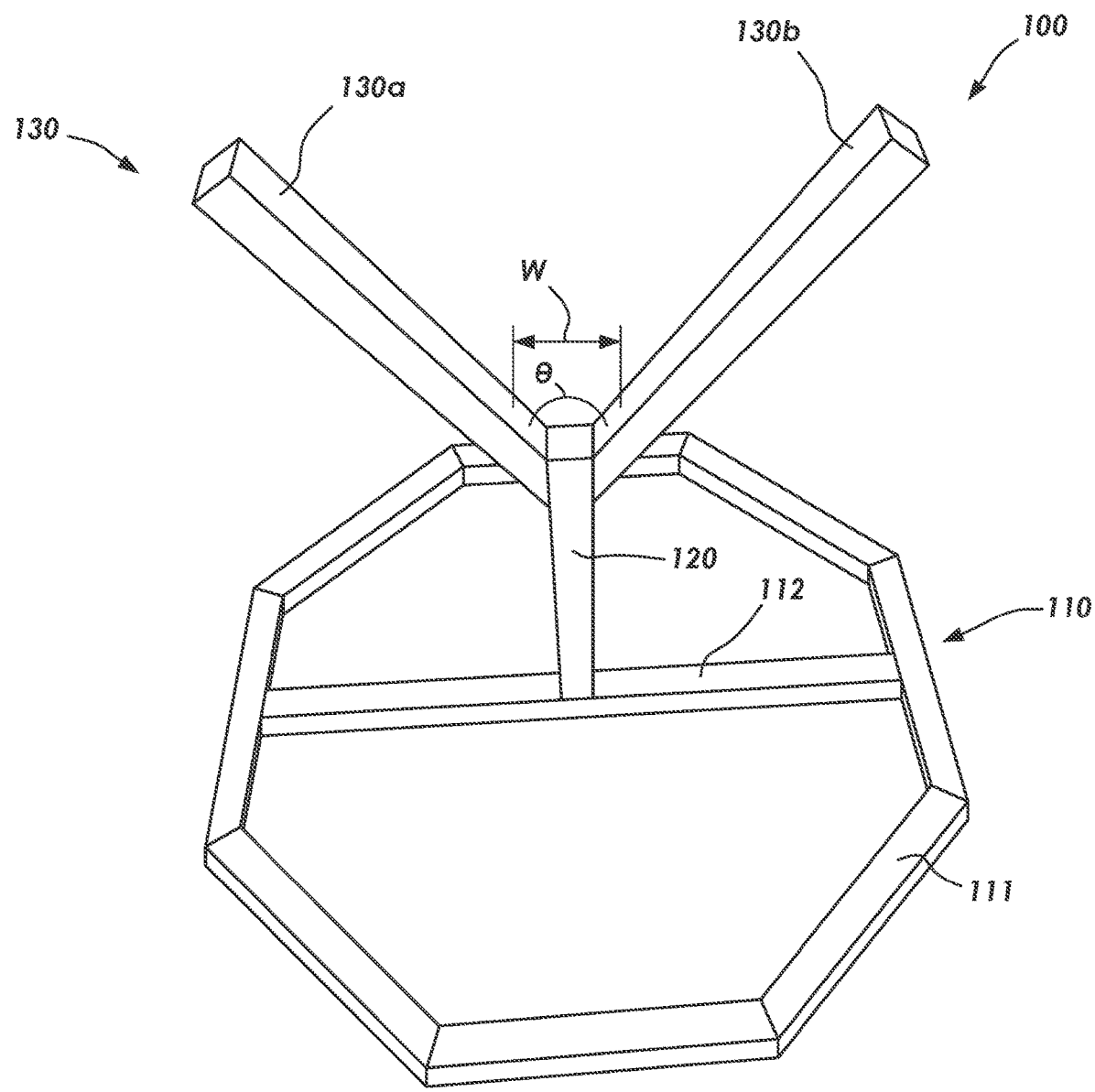
FIG. 1 is a top perspective view of a voluntary euthanasia device according to certain embodiments.

Millions of people worldwide are diagnosed with a terminal illness. Cancer is but one of several illnesses or diseases that can be terminal, which is the person cannot be cured and is likely to lead to death. For example, in the United States alone, there are approximately 1.9 million new cancer diagnoses each year; and of those, there are approximately 609,000 people who die from cancer each year, which is an average of about 1,660 per day. There are other illnesses besides cancer that are incurable and oftentimes terminal, such as dementia and advanced lung, heart, kidney, and liver disease.

People who have been diagnosed with a terminal illness are often left needing increased care—especially near the end of life. Family members or friends may see the level of care needed increase substantially and are not able to provide the level of care that is needed. End-of-life care is designed to make the person's quality of life as bearable as possible, while easing the care family or friends are required to give. Millions of people have utilized hospice or palliative care services.

Unfortunately, even with end-of-life care provided, the quality of life of terminally ill people is often very poor. Pain can be excruciating, and some doctors specialize in pain management specifically for terminally ill people. Even with a specialized doctor providing pain management care through the use of extremely powerful pain killers such as morphine and fentanyl, the pain may never fully abate, and the person is still left suffering from the pain. Other factors negatively affect the overall quality of life for these people.

There are some terminally ill people who desire to have a hastened death instead of living with the pain and poor quality of life and waiting for the disease to naturally progress to death. While it is difficult to determine the actual number of terminally ill people desiring a hastened death, it is estimated that 17% to 45% of people desired to end their life on their own terms. According to the National Institutes of Health, one year after diagnosis, the rate of suicide was 21.6 per 100,000 in low-survival cancer patients versus 9.5 per 100,000 of matched controls. Thus, there can be seen that some percentage of terminally ill people not only desire to hasten death, but actively act on those desires to commit suicide. Moreover, some states have allowed physician-assisted suicide for this group of people. Physician-assisted suicide is generally accomplished when a doctor prescribes or provides medication, that when taken as a lethal dose in the person's home, results in death. However, there are few if any options available to a terminally ill person who wishes to hasten death on their own terms, in their own home, that is guaranteed to result in death, without requiring a doctor to assist. Thus, there is a long-felt need for a voluntary euthanasia device that may be prescribed by a doctor but does not require a doctor's involvement and that can be used in the comfort of the terminally ill person's home or other location.

According to any of the embodiments, a voluntary euthanasia device for a terminally ill person can include: a base; a vertical connector comprising a first end and a second end, wherein the first end is directly or indirectly connected to the base, and wherein the vertical connector extends up from a central location of the base; and a first compression arm and a second compression arm directly connected to the second end of the vertical connector, wherein the first and second compression arms extend up from the second end of the vertical connector and form an angle, and wherein the first and second compression arms are configured to receive a neck of the terminally ill person.

Turning to the figures, FIG. 1 is a top perspective view of the voluntary euthanasia device 100 according to any of the embodiments. Voluntary euthanasia can be defined as the ending of a terminally ill person's life at their behest in order to relieve the person of suffering. The terminally ill person can make this difficult decision on their own or with the support of their family or friends and taking into account information from their doctor. The person can order the voluntary euthanasia device 100 through a medical supply company or other company with or without a doctor's order. In some cases, a doctor may need to order the device and have it shipped to the person or the doctor's office whereby the person or relative can pick up the device from the doctor's office.

The voluntary euthanasia device 100 can include a base 110. The base 110 can be solid or be made of a frame of multiple segments joined together. The base 110 can have a perimeter 111. The perimeter 111 can have a variety of shapes. By way of example, the perimeter 111 can be polygonal, such as octagonal as shown, square, rectangular, circular, oblong, or triangular. The base 110 can have a variety of dimensions. The base 110 can have a largest dimension (i.e., a unit of measure at the widest point such as length, width, or diameter) in a range of 12 to 40 inches. According to any of the embodiments, the largest dimension is selected such that the device has stability when being used and does not fall over when in use. The largest dimension can also be selected depending on whether the device is intended to be used with the base 110 being positioned on the floor or other hard surface or on the person's lap. A smaller largest dimension may be required for use on the person's lap.

A frame base 110 can include multiple segments connected to each other at the ends. By way of example, for a rectangular or square base, there can be a total of 4 segments connected together and for an octagonal base, there can be a total of 8 segments connected together. The segments can have the same length or different lengths, for example for a rectangular base, two segments can be longer than the other two segments. Preferably, the segments are securely connected together such that the base has stability when being used. Depending on the material that the voluntary euthanasia device 100 is made from, the cross member 112 can be connected to the perimeter 111 via screws, nails, or adhesive in the case of wood as the material, or heat welding or spot welding in the case of hard plastics or metals/metal alloys as the material. The segments can have a cross-section selected from circular, square, or rectangular for example.

The base 110 when made of a frame as shown in the drawings, as opposed to being solid, can include a cross member 112. While only shown in FIG. 1 as having one cross member 112, there can also be two or three cross members that are perpendicular to one another or form angles at a center of the base. The cross member 112 can completely span from one edge of the perimeter 111 to the opposite edge of the perimeter 111 through a central location of the base 110 as shown. The cross member 112 can be securely connected to the perimeter 111, for example on the inside of the frame. Depending on the material that the voluntary euthanasia device 100 is made from, the cross member 112 can be connected to the perimeter 111 via screws, nails, or adhesive in the case of wood as the material, or heat welding or spot welding in the case of hard plastics or metals/metal alloys as the material. The cross member 112 can have a cross-section selected from circular, square, or rectangular for example. The cross-section of the cross member 112 can be the same or different from the cross-section of the segments making up the base 110.

The voluntary euthanasia device 100 can also include a vertical connector 120. The vertical connector 120 includes a first end and a second end. The first end is directly or indirectly connected to the base 110. In the case where the base 110 is made of a frame, then the first end of the vertical connector 120 can be indirectly connected to the base via a direct connection to the cross member 112. In the case where the base 110 is solid, then the first end of the vertical connector 120 can be directly connected to a central location of the solid base. The vertical connector 120 can be connected to the base 110 in a similar manner as the discussion pertaining to the connection of the cross member(s) to a frame base, for example depending on the type of material. The length of the vertical connector 120 defined as the distance between the first end and the second end can be in a range of 12 to 24 inches.

The vertical connector 120 extends up from a central location of the base 110 and terminates at the second end of the vertical connector. The vertical connector 120 can extend up from the base 110 such that a longitudinal axis of the vertical connector 120 is perpendicular (i.e., at a 90° angle) from a plane of the base 110. This embodiment can be useful when the voluntary euthanasia device 100 is to be placed on a floor or other solid surface for use. According to other embodiments, for example when the voluntary euthanasia device 100 is to be placed on a terminally ill person's lap for use, the vertical connector 120 can have an angle in relation to the plane of the base that is less than 90° at one side of the perimeter. In other words, the angle can be less than 90° at one side of the perimeter and will thus be greater than 90° at the opposite side of the perimeter. In this manner, the base 110 of the voluntary euthanasia device 100 can be positioned on a user's lap such that the second end of the vertical connector 120 is angled or tilted towards the terminally ill person's head.

The voluntary euthanasia device 100 also includes compression arms 130 connected to the second end of the vertical connector 120. As can be seen in FIG. 1, a first compression arm 130a and a second compression arm 130b are directly connected to the second end of the vertical connector 120. The first and second compression arms 130a/130b extend up from the second end of the vertical connector 120 and form an angle θ at the second end of the vertical connector 120 and are configured to receive a neck of the terminally ill person. By way of example, the angle θ can range from 30° to 110°. The angle θ can be selected based on the neck size of the terminally ill person. By way of example, a person with a neck circumference of 18 inches may benefit from a greater angle, while a person with a neck circumference of 16 inches may benefit from a smaller angle. There will be a width W between an inside edge of the first compression arm 130a and an inside edge of the second compression arm 130b near the location of the second end of the vertical connector 120. The width W can be selected such that the terminally ill person's neck can wholly fit into the first and second compression arms 130a/130b and the person's laryngeal prominence of the thyroid cartilage (also known as an Adam's apple) sits just on top of or very slightly above the second end of the vertical connector 120. The width W can be in a range of 4 to 12 inches. The width W can be varied by varying the angle θ. By way of example, an angle θ of 90° will provide a greater width than an angle θ of 60°. Each of the first and second compression arms 130a/130b can have a length ranging from 6 to 24 inches. Preferably, the length is selected such that there is stability to the compression arms 130 and base 110 of the voluntary euthanasia device 100 during use (i.e., the terminally ill person's head and neck are fully supported in the compression arms 130 and there is little to no risk of the device tipping over or falling during use).

Carotid arteries are part of the circulatory system that supply oxygen-rich blood to organs and tissues in the head and neck including the brain. Approximately 70% of the blood flow going into the brain passes through the carotid arteries. External and internal carotid arteries begin at a carotid bifurcation point on each side of the neck and travel upward along the side of the neck toward the ears. The external carotid arteries supply blood to the face and the internal carotid arteries supply blood into the skull. When there is direct compression of the external and internal carotid arteries and optionally the trachea, oxygen to the brain is severely restricted or prevented. When blood flow to the brain via the carotid arteries is cut off, a person can lose consciousness in a few seconds, and with continued cessation of blood flow to the brain, a person will die in a few minutes. As can be seen, the angle θ of the compression arms 130 form a V shape in relation to the second end of the vertical connector 120. In this manner, direct pressure can be applied to each side of the terminally ill person's neck and optionally trachea to stop blood flow into the brain via the carotid arteries. Accordingly, the angle θ, which also determines the width W, of the compression arms 130 should be selected such that the terminally ill person's trachea is as close to the second end of the vertical connector 120 at the bottom of the V shape as possible and preferably makes contact with the second end and sustained direct pressure is applied to the carotid arteries during use. In this manner, the terminally ill person will be successful in accomplishing their objective of dying.

Any of the components (e.g., for a frame base, the vertical connector, and the compressions arms) of the voluntary euthanasia device 100 can have cross sections selected from square, rectangular, circular, oval, or triangular. The cross-sectional shape can be selected such that enough direct pressure to the carotid arteries is achieved during use such that blood flow into the brain via the internal carotid arteries is completely cut off. If blood flow through the internal carotid arteries is just reduced instead of being completely cut off, then the terminally ill person may not die and instead could wind up having brain damage instead. While a circular or oval cross-section shape may be less hurtful to the person's neck, the cross-sectional shape may need to have 90° edges (e.g., square, rectangular, or triangular cross sections) in order for blood flow to be completely cut off to the brain. The diameter or width of the compression arms 130 may also need to be selected such that pressure is applied to the correct area of the neck to cut off blood flow through the carotid arteries. By way of example, the diameter or width of the compression arms can be selected to span from the terminally ill person's base of the neck just above the collar bones to an area just below the mandible of the face. The diameter or width of the compression arms can range from 3 to 6 inches.

The components of the voluntary euthanasia device 100 can be made from a variety of materials. The material for each of the components is preferably the same as this may be the only means by which to attach or connect one component to another. The material is preferably a rigid material. In this manner, there is stability of the device during use and enough pressure is able to be placed on the carotid arteries and optionally the trachea of the terminally ill person such that blood flow is completely cut off to the brain. The material can be selected from metals, metal alloys, wood, hard plastics, composites, or fiber reinforced resins. Examples of metals include without limitation aluminum, copper, iron, nickel, titanium, or lead. As used herein, the term "metal alloy" means a mixture of two or more elements, wherein at least one of the elements is a metal. The other element(s) can be a non-metal or a different metal. An example of a metal and non-metal alloy is steel, comprising the metal element iron and the non-metal element carbon. An example of a metal and metal alloy is bronze, comprising the metallic elements copper and tin. Preferred metal alloys include without limitation bronze, stainless steel, steel, or bronze or iron alloys. The non-metal elements of the metal alloy can include, but are not limited to, graphite, carbon, silicon, and boron nitride. The wood can be selected from hardwoods such as alder, balsa, beech, hickory, mahogany, maple, oak, teak, and walnut; or softwoods such as cedar, Douglas fir, juniper, pine, redwood, spruce, and yew. Examples of hard plastics include without limitation polyethylene (PE), polypropylene (PP), polystyrene (PS), polyvinyl chloride (PVC), polyethylene terephthalate (PET), low-density polyethylene, polycarbonate (PC), acrylics, and acrylonitrile butadiene styrene (ABS). Examples of suitable composites include, but are not limited to, epoxy-based composites or structural molded phenolics. The epoxy-based composites can be, for example, a glass fiber-reinforced epoxy composite or a carbon fiber-reinforced epoxy composite. The structural molded phenolic can be, for example, thermoplastics or thermoset composite materials.

The components can be solid or hollow. If the material is wood, then the components can be solid. However, depending on the strength of metal, metal alloy, hard plastic, etc., the components can be hollow. For hollow components, the thickness of the components can be selected such that stability is ensured during use and can range from 1/32 of an inch to 1.5 inches. The thickness may need to be increased for materials that have a lower strength to ensure stability during use.

Figure 2:
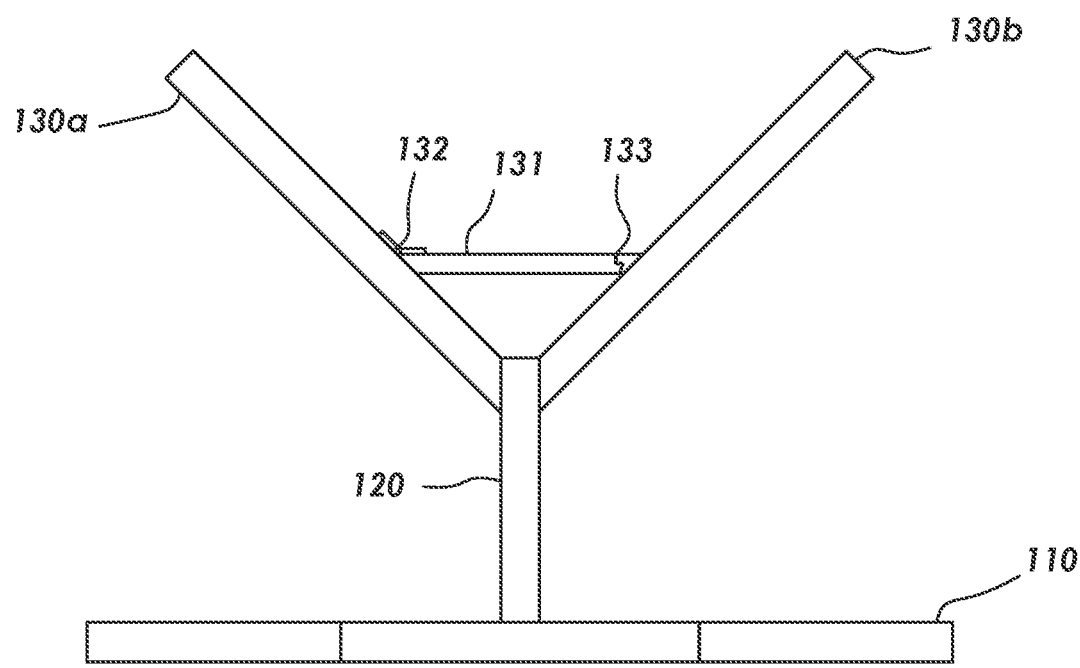
FIG. 2 is a front view of the voluntary euthanasia device according to certain embodiments.
Figure 3:
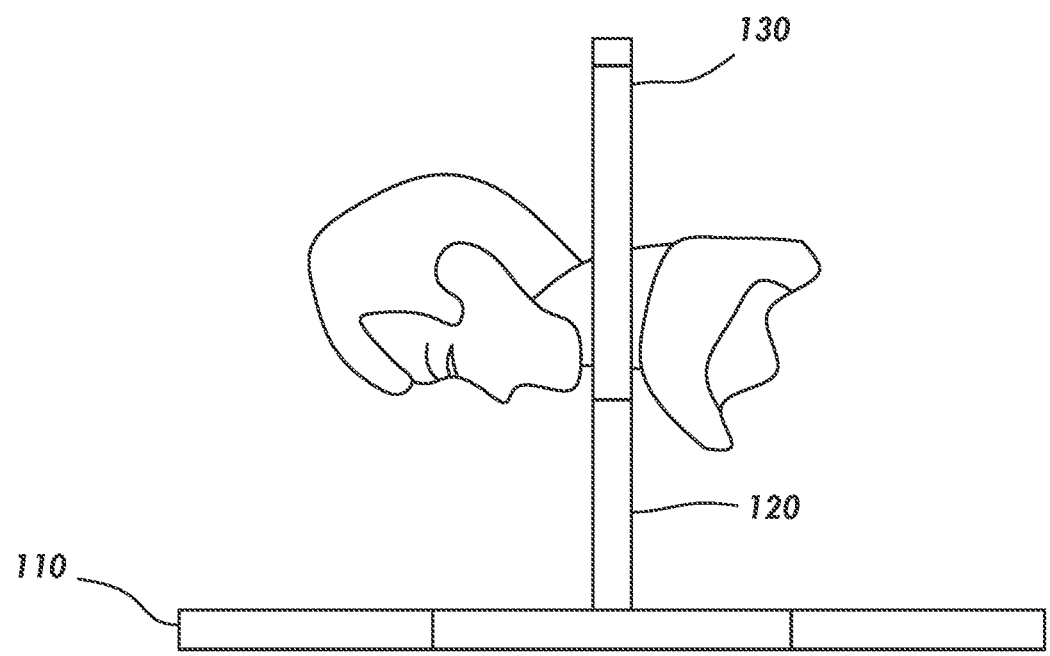
FIG. 3 is a side view of the voluntary euthanasia device with placement of a person's head in the device according to certain embodiments.
Figure 4:
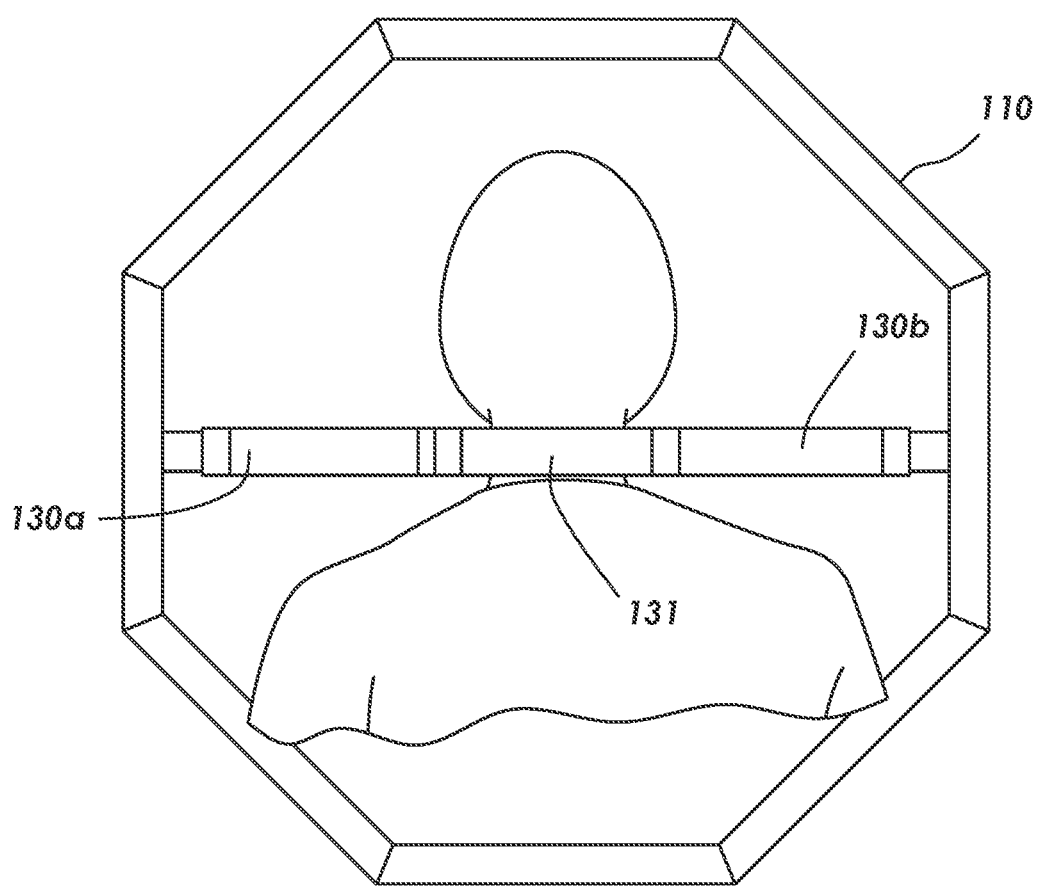
FIG. 4 is a top view of the voluntary euthanasia device with placement of a person's head in the device according to certain embodiments.

Turning to FIGS. 2-4, the voluntary euthanasia device 100 can further include a neck stabilizer. The neck stabilizer can be a locking cross member 131. The locking cross member 131 can be located on the inside edges of the compression arms 130 as shown. The locking cross member 131 can be located along the inside edges at a location that when latched or locked will be located directly on top of the back of the terminally ill person's neck after placement into the compression arms 130. The locking cross member 131 can be connected to the inside of one of the compression arms 130, for example the first or second compression arms 130a/130b via a hinge 132. The hinge 132 can allow the locking cross member 131 to be rotated up to allow placement of the terminally ill person's head and neck into the voluntary euthanasia device 100 and then lowered onto the back of the neck after placement into the device, for example as shown in FIGS. 3 and 4. The other compression arm that is opposite the compression arm with the hinge can include a lock 133. The lock 133 can be any type of mechanism that temporarily prevents the locking cross member 131 from rotating into an open position during use. Examples include without limitation a flip latch, a slide latch, or a spring protrusion and mating hole. Other types of locking cross members can be used and achieve the same purpose. The locking cross member 131 can also be adjustable along the inside edges of the compression arms 130 in order to accommodate different sized necks.

As can be seen in FIG. 3, the terminally ill person can place their neck into the compression arms 130 for use. Gravity will work to apply pressure from the compression arms 130 on the carotid arteries and cut off blood flow to the brain. Within a few seconds, the person will lose consciousness. When the pressure continues to be exerted on the carotid arteries and blood flow is continued to be blocked to the brain, then the terminally ill person will achieve death. However, at the point the terminally ill person loses consciousness, the person's forehead may dip forward towards the ground and the direct contact of the carotid arteries with the compression arms 130 may break. Therefore, in order to maintain this direct contact and ensure that continued pressure is exerted on the carotid arteries, the neck stabilizer can be used to prevent breaking of the direct contact and maintain the necessary pressure exertion. Alternatively, the neck stabilizer can be an adjustable headrest (not shown) that the person can place their forehead into. The headrest may need to be lower than the second end of the vertical connector 120 so enough pressure from the compression arms 130 is exerted onto the carotid arteries to completely cut off blood flow to the brain. By way of another alternative embodiment, another person can assist the terminally ill person to stabilize the neck during use and ensure that the pressure is continuously exerted on the carotid arteries for the length of time necessary to achieve death. By way of another alternative embodiment, the neck stabilizer can be an elastic strap or set of straps (not shown). The elastic straps can be connected to the second end of the vertical connector and designed to be placed over the terminally ill person's head during use, similar to dual elastic straps on surgical masks.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is, therefore, evident that the particular illustrative embodiments disclosed above may be altered or modified and all such variations are considered within the scope and spirit of the present invention.

As used herein, the words "comprise," "have," "include," and all grammatical variations thereof are each intended to have an open, non-limiting meaning that does not exclude additional elements or steps. While compositions, systems, and methods are described in terms of "comprising," "containing," or "including" various components or steps, the compositions, systems, and methods also can "consist essentially of" or "consist of" the various components and steps. It should also be understood that, as used herein, "first," "second," and "third," are assigned arbitrarily and are merely intended to differentiate between two or more compression arms, etc., as the case may be, and does not indicate any sequence. Furthermore, it is to be understood that the mere use of the word "first" does not require that there be any "second," and the mere use of the word "second" does not require that there be any "third," etc.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent(s) or other documents that may be incorporated herein by reference, the definitions that are consistent with this specification should be adopted.

What is claimed is:

1. A euthanasia device for a mammal comprising:
   a base, wherein a plane of the base is configured to be parallel to a plane of the ground when in use, wherein the base has a largest dimension in a range of 12 to 40 inches;
   a vertical connector comprising a first end and a second end, wherein the first end is directly or indirectly connected to a central location of the base, wherein the first end is located directly above a top of the plane of the base, and wherein the vertical connector extends up from the central location of the base and is perpendicular to the plane of the base; and
   a first compression arm and a second compression arm each comprising a first end and a second end, wherein the first ends of the first and second compression arms are directly connected to the second end of the vertical connector, wherein the first and second compression arms extend up from the second end of the vertical connector and form an angle, wherein the second ends of the first and second compression arms form a plane that is parallel to the plane of the base, and wherein the first and second compression arms are configured to receive a neck of the mammal.

2. The euthanasia device according to claim 1, wherein the base is solid.

3. The euthanasia device according to claim 1, wherein the base is a frame made of multiple segments joined together.

4. The euthanasia device according to claim 3, further comprising a cross member, wherein the cross member spans from one of the multiple segments to a segment located on the opposite side from the one segment and through the central location of the base.

5. The euthanasia device according to claim 4, wherein the first end of the vertical connector is indirectly connected to the base via a direct connection to the cross member at the central location of the base.

6. The euthanasia device according to claim 1, wherein the base comprises a perimeter, and wherein the perimeter has a shape selected from square, rectangular, circular, oblong, or triangular.

7. The euthanasia device according to claim 1, wherein the vertical connector has a length defined as the distance between the first end and the second end in a range of 12 to 24 inches.

8. The euthanasia device according to claim 1, wherein the vertical connector extends up from the central location of the base wherein a longitudinal axis of the vertical connector is perpendicular at a 90° angle to a plane of the base.

9. The euthanasia device according to claim 1, wherein a longitudinal axis of the vertical connector has an angle in relation to a plane of the base that is less than 90° at one side of a perimeter of the base.

10. The euthanasia device according to claim 1, wherein the angle formed from the first and second compression arms is in a range of 30° to 110°.

11. The euthanasia device according to claim 1, wherein a width is between an inside edge of the first compression arm and an inside edge of the second compression arm near the location of the second end of the vertical connector.

12. The euthanasia device according to claim 11, wherein the width is in a range of 4 to 12 inches.

13. The euthanasia device according to claim 1, wherein each of the first and second compression arms have a length ranging from 6 to 24 inches, and wherein the length of the first and second compression arms are the same.

14. The euthanasia device according to claim 1, wherein the vertical connector and the first and second compression arms have a cross-sectional shape selected from square, rectangular, circular, oval, or triangular.

15. The euthanasia device according to claim 1, wherein the base, the vertical connector, and the first and second compression arms are made of a material selected from the group consisting of metals, metal alloys, wood, hard plastics, composites, fiber reinforced resins, and combinations thereof.

16. The euthanasia device according to claim 1, further comprising a neck stabilizer.

17. The euthanasia device according to claim 16, wherein the neck stabilizer is a locking cross member.

18. The euthanasia device according to claim 17, wherein a first end of the locking cross member is attached to an inside edge of the first compression arm via a hinge.

19. The euthanasia device according to claim 18, wherein a second end of the locking cross member is releasably connected to an inside edge of the second compression arm via a lock.

* * * * *